United States Patent
Gesing et al.

(10) Patent No.: US 6,297,195 B1
(45) Date of Patent: Oct. 2, 2001

(54) SUBSTITUTED TRIAZOLOAZINE SULPHONAMIDES

(75) Inventors: Ernst Rudolf F. Gesing, Erkrath-Hochdahl; Mark Wilhelm Drewes, Langenfeld; Johannes R. Jansen; Rolf Kirsten, both of Monheim; Joachim Kluth, Langenfeld; Klaus-Helmut Müller, Düsseldorf; Ulrich Philipp, Köln; Hans-Jochem Riebel, Wuppertal; Otto Schallner, Monheim; Detlef Wollweber, Wuppertal, all of (DE); Markus Dollinger, Overland Park, KS (US); Klaus Stenzel, Düsseldorf; Christoph Erdelen, Leichlingen, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/214,773

(22) PCT Filed: Jul. 4, 1997

(86) PCT No.: PCT/EP97/03535

§ 371 Date: May 10, 1999

§ 102(e) Date: May 10, 1999

(87) PCT Pub. No.: WO98/03508

PCT Pub. Date: Jan. 29, 1998

(30) Foreign Application Priority Data

Jul. 19, 1996 (DE) ............................................. 196 29 144

(51) Int. Cl.$^7$ ........................... A01N 43/88; C07D 487/04
(52) U.S. Cl. ........................ 504/223; 504/241; 544/65; 544/263; 514/229.2; 514/258
(58) Field of Search .................. 544/65, 263; 514/229.2; 514/258; 504/223, 241

(56) References Cited

U.S. PATENT DOCUMENTS

| | | | |
|---|---|---|---|
| 4,065,433 | 8/1986 | Pearson et al. | 71/93 |
| 4,605,433 | 8/1986 | Pearson et al. | 71/93 |
| 4,734,123 | 3/1988 | Monte | 71/92 |
| 4,740,233 | 4/1988 | Kleschick et al. | 71/92 |
| 4,741,764 | 5/1988 | Kleschick et al. | 71/92 |
| 4,755,212 | 7/1988 | Kleschick et al. | 71/92 |
| 4,810,282 | 3/1989 | Rorer | 71/90 |
| 4,818,273 | 4/1989 | Kleschick et al. | 71/90 |
| 4,854,964 | 8/1989 | Jelich et al. | 71/92 |
| 4,886,883 | 12/1989 | Kleschick et al. | 544/263 |
| 4,910,306 | 3/1990 | McKendry | 544/263 |
| 4,954,163 * | 9/1990 | Kleschik et al. | 71/92 |
| 4,954,165 | 9/1990 | Baba et al. | 71/103 |
| 4,979,981 | 12/1990 | Pearson et al. | 71/92 |
| 4,983,772 | 1/1991 | Kleschick et al. | 564/442 |
| 5,013,351 | 5/1991 | Jelich et al. | 71/92 |
| 5,015,286 | 5/1991 | Pearson et al. | 71/92 |
| 5,071,468 | 12/1991 | Astles et al. | 71/92 |
| 5,163,995 | 11/1992 | Van Heertum et al. | 71/92 |
| 5,175,289 * | 12/1992 | Schneider et al. | 544/263 |
| 5,217,521 | 6/1993 | Durr | 504/241 |
| 5,559,081 | 9/1996 | Gates et al. | 504/242 |
| 5,700,940 | 12/1997 | Van Heertum et al. | 546/119 |

FOREIGN PATENT DOCUMENTS

| | | |
|---|---|---|
| 3843849 | 7/1990 | (DE) . |
| 0 244 948 | 11/1987 | (EP) . |
| WO 93/16079 | 8/1993 | (WO) . |
| WO93/16079 | 8/1993 | (WO) . |

OTHER PUBLICATIONS

Cron and Hanmond, "Organic Chemistry", McGraw Hill Book Co., NY (1964) 2nd Ed. pp. 565–567.*

Pestic Sci. (month available) 1990, 29, pp. 341–355, New Herbicidal Derivatives of 1,2,4–Triazolo[1,5-α]pyrimidine, William A. Kleschick, Mark J. Costales, Joseph E. Dunbar, Richard W. Meikle, William T. Monte, Norman R. Pearson, Sigrid W. Snider & Anna P. Vinogradoff.

* cited by examiner

Primary Examiner—Patricia L. Morris
(74) Attorney, Agent, or Firm—Joseph C. Gil; Jackie Ann Zurcher

(57) ABSTRACT

The invention concerns novel substituted triazoloazine sulphonamides of formula (I)

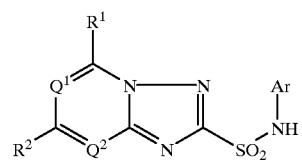

(I)

in which
$Q^1$ stands for nitrogen or a CH group; $Q^2$ stands for nitrogen or a CH group; $R^1$ stands for hydrogen or halogen, or for $C_1$–$C_4$ alkyl, $C_1$–$C_4$ alkoxy, $C_1$–$C_4$ alkylthio, $C_1$–$C_4$ alkylamino or di($C_1$–$C_4$ alkyl)amino, in each case optionally substituted by hydroxy, halogen or $C_1$–$C_4$ alkoxy; $R^2$ stands for hydrogen or halogen, or for $C_1$–$C_4$ alkyl, $C_1$–$C_4$ alkoxy, $C_1$–$C_4$ alkylthio, $C_1$–$C_4$ alkylamino or di($C_1$–$C_4$ alkyl) amino, in each case optionally substituted by halogen; and Ar stands for 4-cyano-2,5-difluoro-phenyl, 2,6-dimethoxy-phenyl, 2-bromo-3-trifluoro-methyl-phenyl, 2-bromo-5-trifluoromethyl-phenyl, 6-chloro-pyridine-3-yl-methyl or one of the 5- or 6-member (hetero)cyclic groups mentioned in the description. The invention also concerns salts of these substances, a process for preparing the novel compounds, and their use as plant-treatment agents.

5 Claims, No Drawings

SUBSTITUTED TRIAZOLOAZINE SULPHONAMIDES

TECHNICAL FIELD OF THE INVENTION

The invention relates to novel substituted triazoloazinesulphonamides, to processes for their preparation and to their use as plant treatment agents.

BACKGROUND OF THE INVENTION

A large number of triazoloazinesulphonamides is already known from the (patent) literature (cf. EP 142152, EP 244847, EP 375076, U.S. Pat. No. 4,605,433, U.S. Pat. No. 5,163,995, WO 89/10368, Pestic. Sci. 29 (1990), 341–355).

DETAILED DESCRIPTION OF THE INVENTION

Novel substituted triazoloazinesulphonamides of the general formula (I)

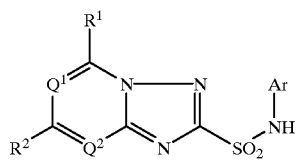

(I)

in which $Q^1$ represents nitrogen or a CH grouping,
$Q^2$ represents nitrogen or a CH grouping,
$R^1$ represents hydrogen, halogen or represents $C_1$–$C_4$-alkyl, $C_1$–$C_4$-alkoxy, $C_1$–$C_4$-alkylthio, $C_1$–$C_4$-alkylamino or di-($C_1$–$C_4$-alkyl)-amino, each of which is optionally substituted by hydroxyl, halogen or $C_1$–$C_4$-alkoxy,
$R^2$ represents hydrogen, halogen or represents $C_1$–$C_4$-alkyl, $C_1$–$C_4$-alkoxy, $C_1$–$C_4$-alkylthio, $C_1$–$C_4$-alkylamino or di-($C_1$–$C_4$-alkyl)-amino, each of which is optionally substituted by halogen, and
Ar represents 4-cyano-2,5-difluoro-phenyl, 2,6-dimethoxy-phenyl, 2-bromo-3-trifluoromethyl-phenyl, 2-bromo-5-trifluoromethyl-phenyl, 4-bromo-2,6-dimethyl-phenyl, 6-chloro-pyridin-3-yl-methyl or one of the 5- or 6-membered (hetero)cyclic groupings below:

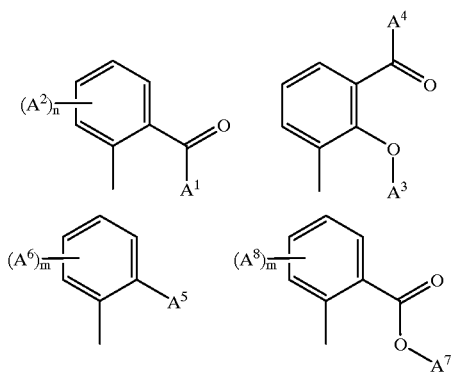

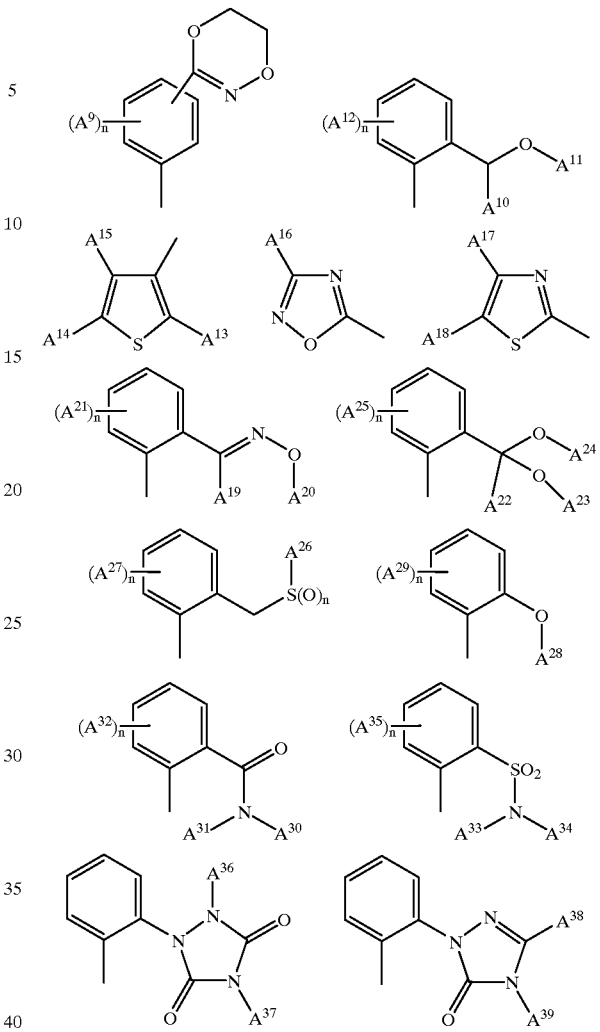

in which
m in each case represents the numbers 1 or 2,
n in each case represents the numbers 0, 1 or 2,
$A^1$ represents optionally cyano-, halogen- or $C_1$–$C_4$-alkoxy-substituted $C_1$–$C_4$-alkyl or represents optionally cyano-, halogen- or $C_1$–$C_4$-alkyl-substituted $C_3$–$C_6$-cycloalkyl,
$A^2$ represents $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl, each of which is optionally substituted by halogen,
$R^3$ represents optionally cyano-, halogen- or $C_1$–$C_4$-alkoxy-substituted $C_1$–$C_4$-alkyl,
$A^4$ represents optionally cyano-, halogen- or $C_1$–$C_4$-alkoxy-substituted $C_1$–$C_4$-alkyl,
$A^5$ represents optionally cyano-, halogen- or $C_1$–$C_4$-alkoxy-substituted $C_2$–$C_4$-alkyl, represents optionally halogen-substituted $C_2$–$C_4$-alkenyl or represents optionally cyano-, halogen- or $C_1$–$C_4$-alkyl-substituted $C_3$–$C_6$-cycloalkyl-$C_1$–$C_4$-alkyl,
$A^6$ represents halogen or represents $C_1$–$C_4$-alkyl, $C_1$–$C_4$-alkoxy, $C_2$–$C_4$-alkenyl or $C_2$–$C_4$-alkenyloxy, each of which is optionally substituted by halogen,
$A^7$ represents cyano-, halogen- or $C_1$–$C_4$-alkoxy-substituted $C_1$–$C_4$-alkyl, $A^8$ represents cyano, nitro or optionally halogen-substituted $C_1$–$C_4$-alkyl, $A^9$ represents cyano, halogen or optionally halogen-substituted $C_1$–$C_4$-alkyl, $A^{10}$ represents optionally cyano-, halogen- or $C_1$–$C_4$-alkoxy-substituted $C_1$–$C_4$-alkyl or represents optionally cyano-, halogen- or $C_1$–$C_4$-alkyl-substituted $C_3$–$C_6$-cycloalkyl, $A^{11}$ represents hydrogen or represents $C_1$–$C_4$-alkyl, $C_1$–$C_4$-alkyl-carbonyl, $C_1$–$C_4$-alkoxycarbonyl or $C_1$–$C_4$-alkylsulphonyl, each of which is optionally substituted by cyano, halogen or $C_1$–$C_4$-alkoxy, $A^{12}$ represents hydrogen, cyano, halogen or optionally halogen-substituted $C_1$–$C_4$-alkyl, $A^{13}$ represents cyano, carbamoyl, 5,6-dihydro-1,4,2-dioxazin-3-yl, halogen, $C_1$–$C_4$-alkyl, $C_1$–$C_4$-alkyl-carbonyl or $C_1$–$C_4$-alkoxy-carbonyl, $A^{14}$ represents hydrogen, represents cyano, carbamoyl, halogen, $C_1$–$C_4$-alkyl, $C_1$–$C_4$-alkylcarbonyl or $C_1$–$C_4$-alkoxy-carbonyl, $A^{15}$ represents hydrogen, represents cyano, carbamoyl, halogen, $C_1$–$C_4$-alkyl, $C_1$–$C_4$-alkylcarbonyl or $C_1$–$C_4$-alkoxy-carbonyl, or together with $A^{14}$ represents a fused benzo grouping, $A^{16}$ represents hydrogen, cyano, halogen or represents $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl, each of which is optionally substituted by halogen, $A^{17}$ represents hydrogen, cyano, halogen or optionally halogen-substituted $C_1$–$C_4$-alkyl, $A^{18}$ represents hydrogen, cyano, halogen or optionally halogen-substituted $C_1$–$C_4$-alkyl, $A^{19}$ represents hydrogen or $C_1$–$C_4$-alkyl, $A^{20}$ represents $C_1$–$C_4$-alkyl or $C_2$–$C_4$-alkenyl, $A^{21}$ represents cyano, halogen, $C_1$–$C_4$-alkyl or $C_1$–$C_4$-halogenoalkyl, $A^{22}$ represents $C_1$–$C_4$-alkyl or $C_1$–$C_4$-halogenoalkyl, $A^{23}$ represents $C_1$–$C_4$-alkyl, $A^{24}$ on its own represents $C_1$–$C_4$-alkyl or together with $A^{23}$ represents $C_2$–$C_4$-alkanediyl, $A^{25}$ represents cyano, halogen, $C_1$–$C_4$-alkyl or $C_1$–$C_4$-halogenoalkyl, $A^{26}$ represents $C_1$–$C_4$-alkyl, $A^{27}$ represents cyano, halogen, $C_1$–$C_4$-alkyl, $C_1$–$C_4$-halogenoalkyl, $C_1$–$C_4$-alkoxy or $C_1$–$C_4$-halogenoalkoxy, $A^{28}$ represents hydrogen, difluoromethyl, $C_1$–$C_4$-alkyl-carbonyl, $C_1$–$C_4$-alkoxy-carbonyl or $C_1$–$C_4$-alkylsulphonyl, $A^{29}$ represents cyano, halogen, $C_1$–$C_4$-alkyl or $C_1$–$C_4$-halogenoalkyl, $A^{30}$ represents hydrogen, $C_1$–$C_4$-alkyl or $C_1$–$C_4$-alkoxy, $A^{31}$ represents hydrogen or $C_1$–$C_4$-alkyl, $A^{32}$ represents cyano, halogen, $C_1$–$C_4$-alkyl or $C_1$–$C_4$-halogenoalkyl, $A^{33}$ represents hydrogen, $C_1$–$C_4$-alkyl or $C_1$–$C_4$-alkoxy, $A^{34}$ represents hydrogen or $C_1$–$C_4$-alkyl, $A^{35}$ represents cyano, halogen, $C_1$–$C_4$-alkyl or $C_1$–$C_4$-halogenoalkyl, $A^{36}$ represents hydrogen, $C_1$–$C_4$-alkyl, $C_3$–$C_6$-cycloalkyl or phenyl, $A^{37}$ represents hydrogen, $C_1$–$C_4$-alkyl, $C_3$–$C_6$-cycloalkyl or phenyl, $A^{38}$ represents hydrogen, halogen, represents $C_1$–$C_4$-alkyl, $C_1$–$C_4$-alkoxy or $C_1$–$C_4$-alkylthio, each of which is optionally substituted by cyano, halogen or $C_1$–$C_4$-alkoxy, or represents $C_3$–$C_6$-cycloalkyl, $C_3$–$C_6$-cycloalkyloxy or $C_3$–$C_6$-cycloalkyl-$C_1$–$C_4$-alkyl, each of which is optionally substituted by cyano, halogen or $C_1$–$C_4$-alkyl, and $A^{39}$ represents hydrogen, represents $C_1$–$C_4$-alkyl or $C_1$–$C_4$-alkoxy, each of which is optionally substituted by cyano, halogen or $C_1$–$C_4$-alkoxy, or represents $C_3$–$C_6$-cycloalkyl, $C_3$–$C_6$-cycloalkyloxy or $C_3$–$C_6$-cycloalkyl-$C_1$–$C_4$-alkyl, each of which is optionally substituted by cyano, halogen or $C_1$–$C_4$-alkyl, and also salts of the compounds of the formula (I) have now been found.

The novel substituted triazoloazinesulphonamides of the general formula (I) are obtained when substituted triazoloazinesulphonyl chlorides of the general formula (II)

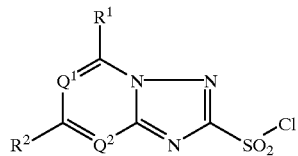

(II)

in which
$Q^1$, $Q^2$, $R^1$ and $R^2$ are each as defined above
are reacted with amino(hetero)arenes of the general formula (III)

$$H_2N\text{---}Ar \qquad (III)$$

in which
Ar is as defined above,
if appropriate in the presence of a reaction auxiliary and if appropriate in the presence of a diluent and, if appropriate, further transformation reactions within the framework of the above definition of substituents are carried out by customary methods on the resulting compounds of the formula (I).

The novel substituted triazoloazinesulphonamides of the general formula (I) have interesting biological properties, allowing their use as plant treatment agents. They have strong herbicidal, fungicidal and insecticidal activity and in particular have excellent and selective herbicidal action.

The invention preferably provides compounds of the formula (I) in which $Q^1$ represents nitrogen or a CH grouping, $Q^2$ represents nitrogen or a CH grouping, $R^1$ represents hydrogen, fluorine, chlorine, bromine or represents methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, each of which is optionally substituted by fluorine, chlorine, methoxy or ethoxy, $R^2$ represents hydrogen, fluorine, chlorine, bromine or represents methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, each of which is optionally substituted by fluorine, chlorine, methoxy or ethoxy, Ar represents 4-cyano-2,5-difluoro-phenyl, 2,6-dimethoxy-phenyl, 2-bromo-3-trifluoromethyl-phenyl, 2-bromo-5-trifluoromethyl-phenyl, 4-bromo-2,6-dimethyl-phenyl, 6-chloro-pyridin-3-yl-methyl or one of the groupings below:

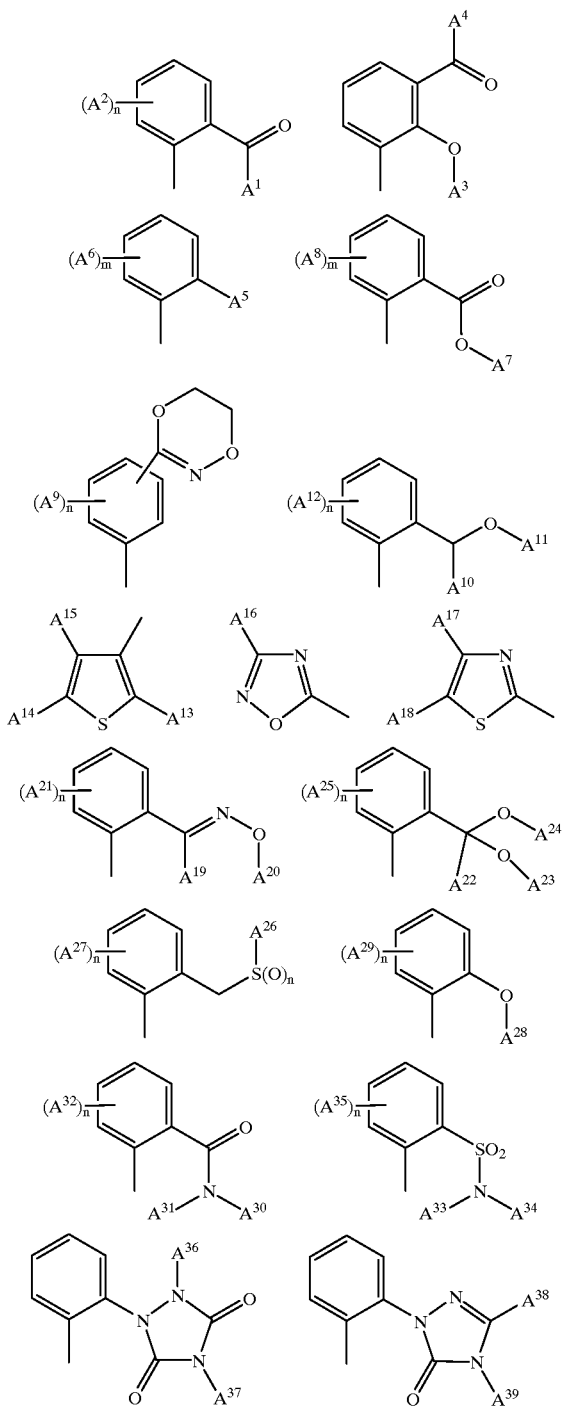

in which
m in each case represents the numbers 1 or 2,
n in each case represents the numbers 0, 1 or 2,
$A^1$ represents methyl, ethyl, n- or i-propyl, each of which is optionally substituted by cyano, fluorine, chlorine, bromine, methoxy or ethoxy, or represents cyclopropyl, cyclobutyl, cyclopentyl or cyclohexyl, each of which is optionally substituted by cyano, fluorine, chlorine, bromine, methyl or ethyl,
$A^2$ represents methyl, ethyl, n- or i-propyl, methoxy, ethoxy, n- or i-propoxy, methylthio, ethylthio, n- or i-propylthio, methylsulphinyl, ethylsulphinyl, n-or i-propylsulphinyl, methylsulphonyl, ethylsulphonyl, n- or i-propylsulphonyl, each of which is optionally substituted by fluorine, chlorine or bromine,
$A^3$ represents methyl, ethyl, n- or i-propyl, each of which is optionally substituted by cyano, fluorine, chlorine, bromine, methoxy or ethoxy,
$A^4$ represents methyl, ethyl, n- or i-propyl, each of which is optionally substituted by cyano, fluorine, chlorine, bromine, methoxy or ethoxy,
$A^5$ represents ethyl, n- or i-propyl, n-, i-, s- or t-butyl, each of which is optionally substituted by cyano, fluorine, chlorine, bromine, methoxy or ethoxy, represents propenyl or butenyl, each of which is optionally substituted by halogen, or cyclopropylmethyl, cyclobutylmethyl, cyclopentylmethyl or cyclohexylmethyl, each of which is optionally substituted by cyano, fluorine, chlorine, bromine, methyl or ethyl,
$A^6$ represents fluorine, chlorine, bromine or represents methyl, ethyl, n- or i-propyl, methoxy, ethoxy, n- or i-propoxy, propenyl, butenyl, propenyloxy or butenyloxy, each of which is optionally substituted by fluorine or chlorine,
$A^7$ represents methyl, ethyl, n- or i-propyl, each of which is optionally substituted by cyano, fluorine, chlorine, bromine, methoxy or ethoxy,
$A^8$ represents cyano, nitro or represents methyl, ethyl, n- or i-propyl, each of which is optionally substituted by fluorine or chlorine,
$A^9$ represents cyano, fluorine, chlorine or represents methyl, ethyl, n- or i-propyl, each of which is optionally substituted by fluorine or chlorine,
$A^{10}$ represents hydrogen, represents methyl, ethyl, n- or i-propyl, each of which is optionally substituted by cyano, fluorine, chlorine, methoxy or ethoxy, or represents cyclopropyl, cyclobutyl, cyclopentyl or cyclohexyl, each of which is optionally substituted by cyano, fluorine, chlorine, methyl or ethyl,
$A^{11}$ represents hydrogen or represents methyl, ethyl, n- or i-propyl, acetyl, propionyl, n- or i-butyroyl, methoxycarbonyl, ethoxycarbonyl, n- or i-propoxycarbonyl, methylsulphonyl, ethylsulphonyl, n- or i-propylsulphonyl, each of which is optionally substituted by cyano, fluorine, chlorine, methoxy or ethoxy,
$A^{12}$ represents hydrogen, cyano, fluorine, chlorine, bromine or represents methyl, ethyl, n- or i-propyl, each of which is optionally substituted by fluorine or chlorine,
$A^{13}$ represents cyano, carbamoyl, 5,6-dihydro-1,4,2-dioxazin-3-yl, fluorine, chlorine, bromine, methyl, ethyl, n- or i-propyl, acetyl, propionyl, n- or i-butyroyl, methoxycarbonyl, ethoxycarbonyl, n- or i-propoxycarbonyl,
$A^{14}$ represents hydrogen, represents cyano, carbamoyl, fluorine, chlorine, bromine, methyl, ethyl, n- or i-propyl, acetyl, propionyl, n- or i-butyroyl, methoxycarbonyl, ethoxycarbonyl, n- or i-propoxycarbonyl,
$A^{15}$ represents hydrogen, represents cyano, carbamoyl, fluorine, chlorine, bromine, methyl, ethyl, n- or i-propyl, acetyl, propionyl, n- or i-butyroyl, methoxycarbonyl, ethoxycarbonyl, n- or i-propoxycarbonyl, or together with $A^{14}$ represents a fused benzo grouping, $A^{16}$ represents hydrogen, cyano, fluorine, chlorine, bromine or represents methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, each of which is optionally substituted by fluorine or chlorine, $A^{17}$ represents hydrogen, cyano, fluorine, chlorine, bromine or represents methyl, ethyl, n- or i-propyl, each of which is optionally substituted by fluorine or chlorine, $A^{18}$ represents hydrogen, cyano, fluorine, chlorine, bromine or represents methyl, ethyl, n- or i-propyl, each of which is optionally substituted by fluorine or chlorine, $A^{19}$ represents hydrogen, methyl, ethyl, n- or i-propyl, $A^{20}$ represents methyl, ethyl, n- or i-propyl or represents propenyl or butenyl, $A^{21}$ represents cyano, fluorine, chlorine, bromine, methyl, ethyl, n- or i-propyl, or represents trifluoromethyl, $A^{22}$ represents methyl, ethyl, n- or i-propyl, $A^{23}$ represents methyl, ethyl, n- or i-propyl, $A^{24}$ on its own represents methyl, ethyl, n- or i-propyl or together with $A^{23}$ represents ethane-1,2-diyl (dimethylene) or propane-1,3-diyl (trimethylene), $A^{25}$ represents cyano, fluorine, chlorine, bromine, methyl, ethyl, n- or i-propyl, or represents trifluoromethyl, $A^{26}$ represents methyl, ethyl, n- or i-propyl, $A^{27}$ represents cyano, fluorine, chlorine, bromine, methyl, ethyl, n- or i-propyl, or represents trifluoromethyl, $A^{28}$ represents hydrogen, acetyl, propionyl, n- or i-butyroyl, methoxycarbonyl, ethoxycarbonyl, n- or i-propoxycarbonyl, methylsulphonyl, ethylsulphonyl, n- or i-propylsulphonyl, $A^{29}$ represents cyano, fluorine, chlorine, bromine, methyl, ethyl, n- or i-propyl, or represents trifluoromethyl, $A^{30}$ represents hydrogen, methyl, ethyl, n- or i-propyl, methoxy, ethoxy, n- or i-propoxy, $A^{31}$ represents hydrogen or methyl, ethyl, n- or i-propyl, $A^{32}$ represents cyano, fluorine, chlorine, bromine, methyl, ethyl, n- or i-propyl, or represents trifluoromethyl, $A^{33}$ represents hydrogen, methyl, ethyl, n- or i-propyl, methoxy, ethoxy, n- or i-propoxy, $A^{34}$ represents hydrogen, methyl, ethyl, n- or i-propyl, $A^{35}$ represents cyano, fluorine, chlorine, bromine, methyl, ethyl, n- or i-propyl, or represents trifluoromethyl, $A^{36}$ represents hydrogen, methyl, ethyl, n- or i-propyl, cyclopropyl, cyclobutyl, cyclopentyl, cyclohexyl or phenyl, $A^{37}$ represents hydrogen, methyl, ethyl, n- or i-propyl, cyclopropyl, cyclobutyl, cyclopentyl, cyclohexyl or phenyl, $A^{38}$ represents hydrogen, fluorine, chlorine, bromine, represents methyl, ethyl, n- or i-propyl, methoxy, ethoxy, n- or i-propoxy, methylthio, ethylthio, n-or i-propylthio, each of which is optionally substituted by cyano, fluorine, chlorine, methoxy or ethoxy, or represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl or cyclohexylmethyl, each of which is optionally substituted by cyano, fluorine, chlorine, methyl or ethyl, and $A^{39}$ represents hydrogen, represents methyl, ethyl, n- or i-propyl, methoxy, ethoxy, n- or i-propoxy, each of which is optionally substituted by cyano, fluorine, chlorine, methoxy or ethoxy, or represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl or cyclohexylmethyl, each of which is optionally substituted by cyano, fluorine, chlorine, methyl or ethyl.

The invention also preferably provides lithium, sodium, potassium, magnesium, calcium, ammonium, $C_1$–$C_4$-alkyl-ammonium, di-($C_1$–$C_4$-alkyl)-ammonium, tri-($C_1$–$C_4$)-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I).

The above-mentioned general or preferred radical definitions apply both to the end products of the formula (I) and also, correspondingly, to the starting materials or intermediates required in each case for the preparation. These radical definitions can be combined with each other as desired, i.e. including combinations between the given ranges.

Using, for example, 5,7-dimethyl-1,2,4-triazolo[1,5-a] pyrimidine-2-sulphonyl chloride and 2-amino-phenol as starting materials, the course of the reaction in the process according to the invention can be illustrated by the following equation:

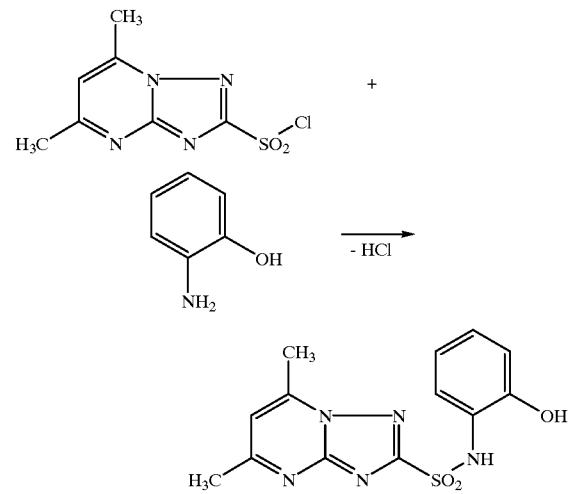

The formula (II) provides a general definition of the triazoloazinesulphonyl chlorides to be used as starting materials in the process according to the invention for preparing compounds of the formula (I). In the formula (II), $Q^1$, $Q^2$, $R^1$ and $R^2$ each preferably have those meanings which have already been indicated above, in connection with the description of the compounds of the formula (I) according to the invention, as being preferred for $Q^1$, $Q^2$, $R^1$ and $R^2$.

The starting materials of the formula (II) are known and/or can be prepared by processes known per se (cf. EP 142152, EP 244847, EP 375076, U.S. Pat. No. 4,605,433, U.S. Pat. No. 5,163,995, WO 89/10368).

The formula (III) provides a general definition of the amino(hetero)arenes further to be used as starting materials in the process according to the invention. In the formula (III), Ar preferably has that meaning which has already been indicated above, in connection with the description of the compounds of the formula (I) according to the invention, as being preferred for Ar.

The starting materials of the formula (III) are known and/or can be prepared by processes known per se (cf. EP 142152, EP 244847, EP 375076, U.S. Pat. No. 4,605,433, U.S. Pat. No. 5,163,995, WO 89/10368).

Suitable reaction auxiliaries for the process according to the invention are generally the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds, such as, for example, trimethylamine, triethylamine, tripropylamine, tributylamine, ethyldiisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methylpiperidine, 1,4-diazobicyclo[2.2.2]-octane (DABCO), 1,5-diazabicyclo[4.3.0]-non-5-ene (DBN), or 1,8-diazabicyclo[5.4.0]-undec-7-ene (DBU).

Suitable diluents for carrying out the process according to the invention are in particular inert organic solvents. These preferably include aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate; sulphoxides, such as dimethyl sulphoxide; alcohols, such as methanol, ethanol, n- or i-propanol, ethylene glycol monomethyl ether, ethylene glycol monoethyl-ether, diethylene glycol monomethyl ether, diethylene glycol monoethyl ether, mixtures thereof with water or pure water.

When carrying out the process according to the invention, the reaction temperatures can be varied within a relatively wide range. In general, the reaction is carried out at temperatures between 0° C. and 100° C., preferably between 10° C. and 60° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to employ one of the components in a relatively large excess. The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds of the formula (I) according to the invention can be used as defoliants, desiccants, haulm killers and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial crops, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land and for the selective control of weeds in annual crops.

The compounds of the formula (I) according to the invention are particularly suitable for the selective control of monocotyledonous and dicotyledonous weeds in monocotyledonous and dicotyledonous crops, both pre-emergence and post-emergence.

The active compounds of the formula (I) according to the invention to a certain extent also have strong microbicidal action and can be practically employed for controlling undesirable microorganisms. The active compounds are consequently also suitable for use as fungicides and bactericides.

Fungicides in plant protection are employed for controlling Plasmodiophoromycetes, Oomycetes, Chytridiomycetes, Zygomycetes, Ascomycetes, Basidiomycetes and Deuteromycetes.

Bactericides in plant protection are employed for controlling Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Xanthomonas species, such as *Xanthomonas campestris pv. oryzae;* Pseudomonas species, such as *Pseudomonas syringae pv. lachrymans;* Erwinia species, such as *Erwinia amylovora;* Pythium species, such as *Pythium ultimum;* Phytophthora species, such as *Phytophthora infestans;* Pseudoperonospora species, such as *Pseudoperonospora humuli* or *Pseudoperonospora cubensis;* Plasmopara species, such as *Plasmopara viticola;* Bremia species, such as *Bremia lactucae;* Peronospora species, such as *Peronospora pisi* or *P. brassicae;* Erysiphe species, such as *Erysiphe graminis;* Sphaerotheca species, such as *Sphaerotheca fuliginea;* Podosphaera species, such as *Podosphaera leucotricha;* Venturia species, such as *Venturia inaequalis;* Pyrenophora species, such as *Pyrenophora teres* or *P. graminea* (conidia form: Drechslera, syn: Helminthosporium); Cochliobolus species, such as *Cochliobolus sativus* (conidia form: Drechslera, syn: Helminthosporium); Uromyces species, such as *Uromyces appendiculatus;* Puccinia species, such as *Puccinia recondita;* Scierotinia species, such as *Sclerotinia sclerotiorum;* Tilletia species, such as *Tilletia caries;* Ustilago species, such as *Ustilago nuda* or *Ustilago avenae;* Pellicularia species, such as *Pellicularia sasakii;*

Pyricularia species, such as *Pyricularia oryzae;* Fusarium species, such as *Fusarium culmorum;* Botrytis species, such as *Botrytis cinerea;* Septoria species, such as *Septoria nodorum;* Leptosphaeria species, such as *Leptosphaeria nodorum;* Cercospora species, such as *Cercospora canescens;* Altemaria species, such as *Alternaria brassicae;* Pseudocercosporella species, such as *Pseudocercosporella herpotrichoides.*

The good toleration, by plants, of some of the active compounds, at the concentrations required for controlling plant diseases, permits treatment of aerial parts of plants, of vegetative propagation stock and seeds, and of the soil.

The active compounds according to the invention can be employed here very successfully for controlling diseases in fruit and vegetable growing, such as, for example, against Podosphaera and Sphaerotheca species, and also for controlling rice diseases, such as, for example, Pyricularia oryzae.

The active compounds of the formula (I) according to the invention are to a certain extent also suitable for controlling animal pests, preferably arthropods and nematodes, in particular insects and arachnids which are encountered in agriculture, in forests, in the protection of stored products and of materials, and in the hygiene sector. They are active against normally sensitive and resistant species and against all or some stages of development. The above-mentioned pests include:

From the order of Isopoda, for example, *Oniscus asellus, Armadillidium vulgare* and *Porcellio scaber;* from the order of the Diplopoda, for example, *Blaniulus guttulatus;* from the order of the Chilopoda, for example, *Geophilus carpophagus* and Scutigera spec; from the order of the Symphyla, for example, *Scutigerella immaculata;* from the order of the Thysanura, for example, *Lepisma saccharina;* from the order of the Collembola, for example, *Onychiurus armatus;* from the order of the Orthoptera, for example, *Blatta orientalis, Periplaneta americana, Leucophaea maderae, Blatella germanica, Acheta domesticus,* Gryllotalpa spp., *Locusta migratoria migratorioides, Melanoplus differentialis* and *Schistocerca gregaria;* from the order of the Dermaptera, for example, *Forficula auricularia;* from the order of the Isoptera, for example, Reticulitermes spp.; from the order of the Anoplura, for example, *Pediculus humanus corporis,* Haematopinus spp. and Linognathus spp; from the order of the Mallophaga, for example, Trichodectes spp. and Damalinea spp; from the order of the Thysanoptera, for example, *Hercinothrips femoralis* and *Thrips tabaci;* from the order of the Heteroptera, for example, Eurygaster spp., *Dysdercus intermedius, Piesma quadrata, Cimex lectularius, Rhodnius prolixus* and Triatoma spp.; from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis,* Macrosiphum avenae, Myzus spp., Pemphigus spp., *Phorodon humuli, Phylloxera vastatrix, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example, Diprion spp., Hoplocampa spp., Lasius spp., *Monomorium pharaonis* and Vespa spp.; from the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example, *Xenopsylla cheopis* and Ceratophyllus spp; from the order of the Arachnida, for example, *Scorpio maurus* and *Latrodectus mactans;* from the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp. The phytoparasitic nematodes include, for example, Pratylenchus spp., Radopholus spp., Ditylenchus spp., Tylenchulus spp., Heterodera spp., Globodera spp., Meloidogyne spp., Aphelenchoides spp., Longidorus spp., Xiphinema spp., Trichodorus spp., Tylenchus spp., Helicotylenchus spp., Rotylenchus spp., Tylenchulus spp.

The active compounds according to the invention can be employed here very successfully, for example, against butterfly larvae, such as, for example, *Plutella maculipennis.*

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; as dispersing agents there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be used as such or, in their formulations, also as a mixture with known herbicides for the control of weeds, in which case ready-to-use formulations or tank mixes are possible.

Suitable co-components for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxyphenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiolcarbamates such as, for example, butylates, cycloates, di-allates, EPTC, esprocarb, molinates, prosulfocarb, thiobencarb and triallates; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the application rates are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

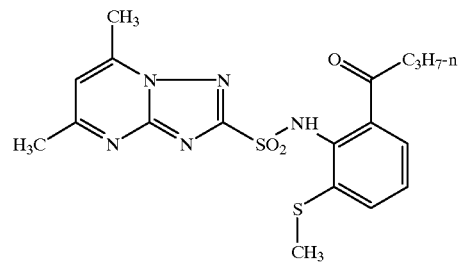

At room temperature (approximately 20° C.), a mixture of 2.1 g (10 mmol) of 2-methylthio-6-n-butyroyl-aniline, 2.5 g (10 mmol) of 5,7-dimethyl-1,2,4-triazolo[1,5-a]pyrimdine-2-sulphonyl chloride and 30 ml of pyridine is stirred for approximately 15 hours. The pyridine is subsequently carefully distilled off under water pump vacuum and the residue is taken up with 100 ml of methylene chloride and washed twice each with 2N hydrochloric acid and with water, dried with magnesium sulphate and filtered. The filtrate is concentrated under water pump vacuum, the amorphous residue is crystallized by treatment with ethanol and the product is isolated by filtration with suction.

This gives 2.8 g (67% of theory) of 5,7-dimethyl-N-(2-methylthio-6-n-butyroyl-phenyl)-1,2,4-triazolo[1,5-a]pyrimidine-2-sulphonamide of melting point 138° C.

Example 2

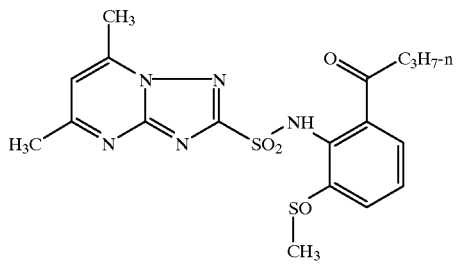

3.2 g (7.5 mmol) of 5,7-dimethyl-N-(2-methylthio-6-n-butyroyl-phenyl)- 1,2,4-triazolo[1,5-a]pyrimidine-2-sulphonamide are initially charged in 60 ml of chloroform, and the solution is admixed with 1.8 g of 3-chloroperbenzoic acid (70% strength). The reaction mixture is then stirred at room temperature (approximately 20° C.) for approximately 60 minutes and subsequently concentrated under water pump vacuum. The residue is digested with 40 ml of ethanol and the resulting crystalline product is isolated by filtration with suction.

This gives 2,3 g (70% of theory) of 5,7-dimethyl-N-(2-methylsulphinyl-6-n-butyroyl-phenyl)-1,2,4-triazolo[1,5-a]pyrimidine-2-sulphonamide of melting point 255° C. (with decomposition).

Example 3

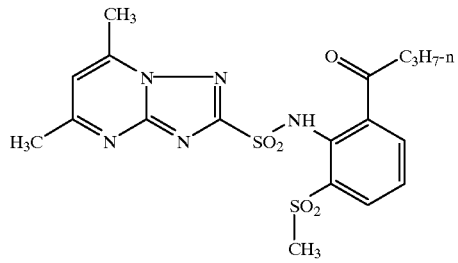

2.1 g (5 mmol) of 5,7-dimethyl-N-(2-methylthio-6-n-butyroyl-phenyl)- 1,2,4-triazolo[1,5-a]pyrimidine-2-sulphonamide are initially charged in 50 ml of chloroform, and the solution is admixed with 2.8 g of 3-chloroperbenzoic acid (70% strength). The reaction mixture is then stirred at room temperature (approximately 20° C.) for approximately 2 hours and subsequently concentrated under water pump vacuum. The residue is digested with 30 ml of ethanol and the resulting crystalline product is isolated by filtration with suction.

This gives 2.0 g (89% of theory) of 5,7-dimethyl-N-(2-methylsulphonyl-6-n-butyroyl-phenyl)-1,2,4-triazolo[1,5-a]pyrimidine-2-sulphonamide of melting point 236° C. (with decomposition).

Similarly to the Preparation Examples 1 to 3, and in accordance with the general description of the preparation processes according to the invention, it is also possible to prepare, for example, the compounds of the formula (I) listed in Table 1 below.

TABLE 1

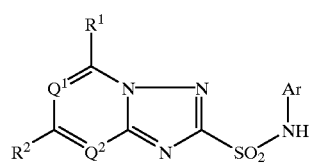

(I)

Examples of compounds of the formula (I)

| Ex. No. | $Q^1$ | $Q^2$ | $R^1$ | $R^2$ | Ar | Melting point (° C.) |
|---|---|---|---|---|---|---|
| 4 | CH | N | $CH_3$ | $CH_3$ | 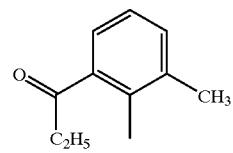 | 169 |
| 5 | CH | N | $CH_3$ | $CH_3$ | 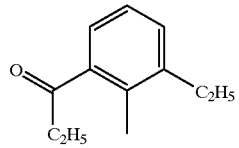 | 218 |

TABLE 1-continued
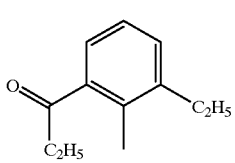
Examples of compounds of the formula (I)
| Ex. No. | Q¹ | Q² | R¹ | R² | Ar | Melting point (° C.) |
|---|---|---|---|---|---|---|
| 6 | CH | N | CF$_3$ | CH$_3$ | 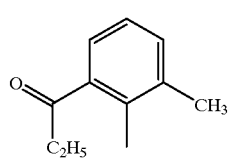 | 179 |
| 7 | CH | N | CF$_3$ | CF$_3$ | 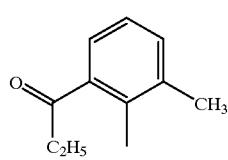 | 102 |
| 8 | CH | N | CF$_3$ | CH$_3$ | 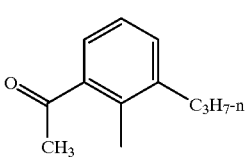 | 206 |
| 9 | CH | N | CH$_3$ | CH$_3$ | 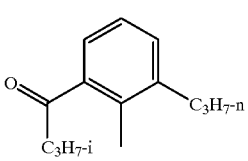 | 179 |
| 10 | CH | N | CH$_3$ | CH$_3$ | 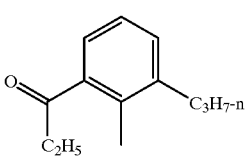 | 146 |
| 11 | CH | N | CH$_3$ | CH$_3$ | 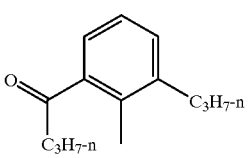 | 155 |
| 12 | CH | N | CH$_3$ | CH$_3$ | (C$_3$H$_7$-n, C$_3$H$_7$-n) | 111 |

TABLE 1-continued

Examples of compounds of the formula (I)

(I)

| Ex. No. | Q¹ | Q² | R¹ | R² | Ar | Melting point (° C.) |
|---|---|---|---|---|---|---|
| 13 | CH | N | CH₃ | CH₃ | 3-(n-C₃H₇)-2-CH₃-phenyl with cyclopropyl ketone at position 1 | 181 |
| 14 | CH | N | CH₃ | CH₃ | 3-OCH₃-2-CH₃-phenyl with CH₃ ketone at position 1 | 201 |
| 15 | CH | N | CH₃ | CH₃ | 3-OCH₃-2-CH₃-phenyl with C₂H₅ ketone at position 1 | 186 |
| 16 | CH | N | CH₃ | CH₃ | 3-OC₂H₅-2-CH₃-phenyl with C₂H₅ ketone at position 1 | 178 |
| 17 | CH | N | CH₃ | CH₃ | 3-CH₃-2-CH₃-phenyl with cyclopropyl ketone at position 1 | 235 |
| 18 | CH | N | CH₃ | CH₃ | 3-CH₃-2-CH₃-phenyl with CH₃ ketone at position 1 | 258 |
| 19 | CH | N | CH₃ | CH₃ | 3,4-di-CH₃-2-CH₃-phenyl with C₂H₅ ketone at position 1 | 248 |

TABLE 1-continued
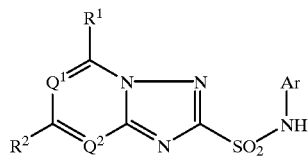
Examples of compounds of the formula (I)
| Ex. No. | Q¹ | Q² | R¹ | R² | Ar | Melting point (° C.) |
|---|---|---|---|---|---|---|
| 20 | CH | N | CF$_3$ | CH$_3$ | 4-CH$_3$, 3-CH$_3$, 2-C$_2$H$_5$ benzoyl | 184 |
| 21 | CH | N | CH$_3$ | CH$_3$ | 4-Cl, 3-CH$_3$, 2-C$_2$H$_5$ benzoyl | 182 |
| 22 | CH | N | CH$_3$ | CH$_3$ | 4-Cl, 3-CH$_3$, 2-cyclopropyl benzoyl | 193 |
| 23 | CH | N | CH$_3$ | CH$_3$ | 4-Cl, 3-CH$_3$, 2-CH$_3$ benzoyl | 186 |
| 24 | CH | N | CH$_3$ | CH$_3$ | 4-Br, 3-CH$_3$, 2-C$_2$H$_5$ benzoyl | 184 |
| 25 | CH | N | CH$_3$ | CH$_3$ | 4-F, 3-CH$_3$, 2-C$_2$H$_5$ benzoyl | 168 |
| 26 | CH | N | CH$_3$ | CH$_3$ | 2-CH$_3$, cyclopropyl benzoyl | 172 |

TABLE 1-continued
Examples of compounds of the formula (I)
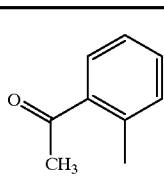
| Ex. No. | Q¹ | Q² | R¹ | R² | Ar | Melting point (° C.) |
|---|---|---|---|---|---|---|
| 27 | CH | N | CH₃ | CH₃ | 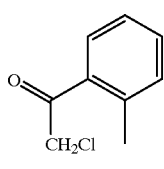 | 179 |
| 28 | CH | N | CH₃ | CH₃ | 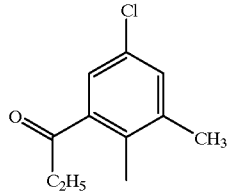 | 245 |
| 29 | CH | N | CH₃ | CH₃ | 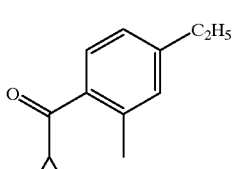 | 197 |
| 30 | CH | N | CH₃ | CH₃ | 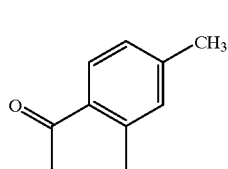 | 135 |
| 31 | CH | N | CH₃ | CH₃ | 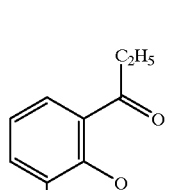 | 159 |
| 32 | CH | N | CH₃ | CH₃ |  | 177 |

TABLE 1-continued
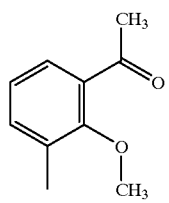
Examples of compounds of the formula (I)
| Ex. No. | Q¹ | Q² | R¹ | R² | Ar | Melting point (° C.) |
|---|---|---|---|---|---|---|
| 33 | CH | N | CH₃ | CH₃ | 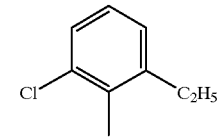 | 246 |
| 34 | CH | N | CH₃ | CH₃ | 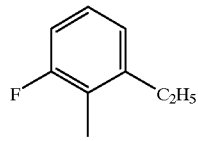 | 234 |
| 35 | CH | N | CH₃ | CH₃ | 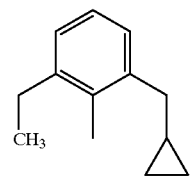 | 238 |
| 36 | CH | N | CH₃ | CH₃ | 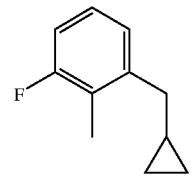 | 210 |
| 37 | CH | N | CH₃ | CH₃ | 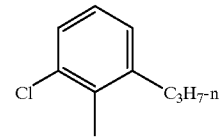 | 246 |
| 38 | CH | N | CH₃ | CH₃ | 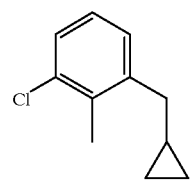 | 225 |
| 39 | CH | N | CH₃ | CH₃ | | 254 |

TABLE 1-continued
Examples of compounds of the formula (I)
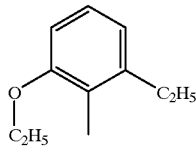
| Ex. No. | $Q^1$ | $Q^2$ | $R^1$ | $R^2$ | Ar | Melting point (° C.) |
|---|---|---|---|---|---|---|
| 40 | CH | N | $CH_3$ | $CH_3$ | 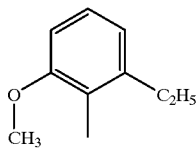 | 179 |
| 41 | CH | N | $CH_3$ | $CH_3$ | 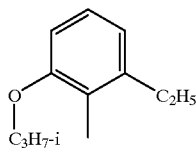 | 234 |
| 42 | CH | N | $CH_3$ | $CH_3$ | 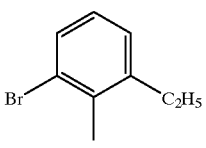 | 206 |
| 43 | CH | N | $CH_3$ | $CH_3$ | 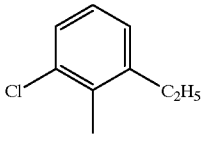 | 224 |
| 44 | CH | N | $CH_2OH$ | $CH_3$ | 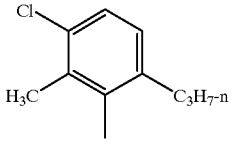 | 206 |
| 45 | CH | N | $CH_3$ | $CH_3$ | 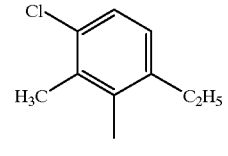 | 207 |
| 46 | CH | N | $CH_3$ | $CH_3$ |  | 277 |

TABLE 1-continued $$(I)$$

Examples of compounds of the formula (I)

| Ex. No. | $Q^1$ | $Q^2$ | $R^1$ | $R^2$ | Ar | Melting point (°C.) |
|---|---|---|---|---|---|---|
| 47 | CH | N | $CH_3$ | $CH_3$ | 4-Cl, 3-$CH_3$, 2-(cyclopropylmethyl)phenyl | 218 |
| 48 | CH | N | $CH_3$ | $CH_3$ | 4-F, 3-$CH_3$, 2-$C_3H_7$-n phenyl | 205 |
| 49 | CH | N | $CH_3$ | $CH_3$ | 4-Br, 3-$CH_3$, 2-$C_3H_7$-n phenyl | 204 |
| 50 | CH | N | $CH_3$ | $CH_3$ | 3-Cl, 2-$CH_3$, (vinyl)phenyl | 233 |
| 51 | CH | N | $CH_3$ | $CH_3$ | 5-Cl, 3-$CH_3$, 2-$C_3H_7$-n phenyl | 168 |
| 52 | CH | N | $CH_3$ | $CH_3$ | 3,5-Br, 4-$CH_3$, 2-$C_2H_5$ phenyl | 239 |
| 53 | CH | N | $CH_3$ | $CH_3$ | 5-Br, 3-$OCH_3$, 2-$C_2H_5$ phenyl | 217 |

TABLE 1-continued

Examples of compounds of the formula (I)

| Ex. No. | Q$^1$ | Q$^2$ | R$^1$ | R$^2$ | Ar | Melting point (° C.) |
|---|---|---|---|---|---|---|
| 54 | CH | N | CH$_3$ | CH$_3$ | 2,5-dimethoxy-3-ethyl-4-methylphenyl | 224 |
| 55 | CH | N | CH$_3$ | CH$_3$ | 3,5-dibromo-2-methyl-4-n-propylphenyl... (3,5-dibromo-4-methyl-with C$_3$H$_7$-n) | 226 |
| 56 | CH | N | CH$_3$ | CH$_3$ | 5-bromo-2-methyl-3-ethylphenyl | 219 |
| 57 | CH | N | CH$_3$ | CH$_3$ | 5-chloro-2-methyl-3-ethylphenyl | 231 |
| 58 | CH | N | CH$_3$ | CH$_3$ | 3-methyl-2-methyl-... n-propylphenyl | 237 |
| 59 | CH | N | CH$_3$ | CH$_3$ | 3-methyl-2-methyl-(cyclopropylmethyl)phenyl | 256 |

TABLE 1-continued

Examples of compounds of the formula (I)

| Ex. No. | Q¹ | Q² | R¹ | R² | Ar | Melting point (° C.) |
|---|---|---|---|---|---|---|
| 60 | CH | N | CH₃ | CH₃ | 3-methyl-2-methyl-phenyl with C(O)OCH₂CF₃ | 154 |
| 61 | CH | N | CF₃ | CH₃ | 3-methyl-2-methyl-phenyl with C(O)OCH₂CF₃ | 101 |
| 62 | CH | N | CH₃ | CH₃ | 2-methylphenyl with 1,4,2-dioxazine | |
| 63 | CH | N | CH₃ | CH₃ | 3-methyl-2-methyl-phenyl with 1,4,2-dioxazine | |
| 64 | CH | N | CH₃ | CH₃ | 3-methyl-2-methyl-phenyl with 1,5,2-dioxazine | |
| 65 | CH | N | CH₃ | CH₃ | 3-methyl-2-methyl-phenyl with CH(C₂H₅)OH | 222 |
| 66 | CH | N | CH₃ | CH₃ | 3-methyl-2-methyl-phenyl with CH(C₂H₅)OSO₂CH₃ | 245 |

TABLE 1-continued

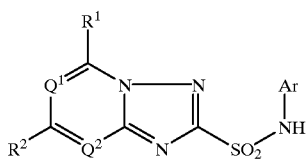

Examples of compounds of the formula (I)

| Ex. No. | Q¹ | Q² | R¹ | R² | Ar | Melting point (° C.) |
|---|---|---|---|---|---|---|
| 67 | CH | N | CF$_3$ | CF$_3$ | 2,3-dimethylphenyl-CH(OH)(C$_2$H$_5$) | 88 |
| 68 | CH | N | CH$_3$ | CH$_3$ | 2,3,4-trimethylphenyl-CH(OH)(C$_2$H$_5$) | 237 |
| 69 | CH | N | CH$_3$ | CH$_3$ | 3-methyl-2-acetylthiophene | 111 |
| 70 | CH | N | CH$_3$ | CH$_3$ | 3-methyl-2-carbamoylthiophene | 214 |
| 71 | CH | N | CH$_3$ | CH$_3$ | 3-chloro-5-methyl-1,2,4-oxadiazole | 112 |
| 72 | CH | N | CH$_3$ | CH$_3$ | 4-chloro-5-cyano-2-methylthiazole | 59 |
| 73 | CH | N | CH$_3$ | CH$_3$ | 3,4-dimethyl-2-(methoxycarbonyl)thiophene | 222 |
| 74 | CH | N | CH$_3$ | CH$_3$ | 2,3,4-trimethylthiophene | 246 |

TABLE 1-continued

Examples of compounds of the formula (I)

(I)

| Ex. No. | $Q^1$ | $Q^2$ | $R^1$ | $R^2$ | Ar | Melting point (° C.) |
|---|---|---|---|---|---|---|
| 75 | CH | N | $CF_3$ | $CH_3$ | 3,4-dimethylthiophene-2-C(O)OCH$_3$ | 187 |
| 76 | CH | N | $CH_3$ | $CH_3$ | 3,4-dimethylthiophene-2-C(O)OC$_2$H$_5$ | 172 |
| 77 | CH | N | $CH_3$ | $CH_3$ | 3,4-dimethylthiophene-2-C(O)OC$_3$H$_7$-i | 101 |
| 78 | CH | N | $CH_3$ | $CH_3$ | 3,4-dimethylthiophene-2-C(O)OC$_3$H$_7$-n | 90 |
| 79 | CH | N | $CH_2OCH_3$ | $CH_3$ | 3-methylbenzothiophene-2-C(O)OC$_2$H$_5$ | — |
| 80 | CH | N | $CH_2OCH_3$ | $CH_3$ | 4-methylthiophene-2,3-di-C(O)OCH$_3$ | 89 |

TABLE 1-continued
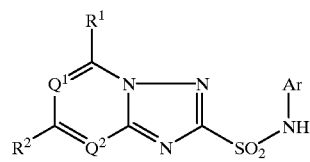
(I)
Examples of compounds of the formula (I)
| Ex. No. | Q¹ | Q² | R¹ | R² | Ar | Melting point (° C.) |
|---|---|---|---|---|---|---|
| 81 | CH | N | CH₃ | CH₃ | 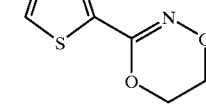 | |
| 82 | CH | N | CH₃ | CH₃ | 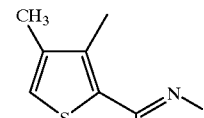 | |
| 83 | CH | N | CF₃ | CH₃ | 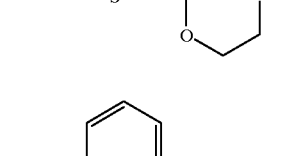 | 179 |
| 84 | CH | N | CH₃ | CH₃ | 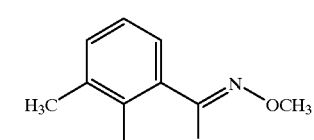 | 192 |
| 85 | CH | N | CH₃ | CH₃ | 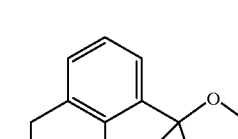 | 186 |
| 86 | CH | N | CH₃ | CH₃ | 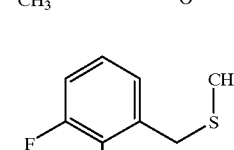 | 209 |
| 87 | CH | N | CH₃ | CH₃ | 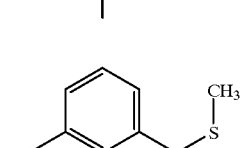 | 223 |

TABLE 1-continued

Examples of compounds of the formula (I)

| Ex. No. | Q¹ | Q² | R¹ | R² | Ar | Melting point (° C.) |
|---|---|---|---|---|---|---|
| 88 | CH | N | $CH_3$ | $CH_3$ | 3-ethoxy-2-methyl-6-(methylthiomethyl)phenyl | 161 |
| 89 | CH | N | $CH_3$ | $CH_3$ | 3-bromo-2-methyl-6-(methylthiomethyl)phenyl | 206 |
| 90 | CH | N | $CH_3$ | $CH_3$ | 3-isopropyl-2-methyl-6-(methylthiomethyl)phenyl | 226 |
| 91 | CH | N | $CH_3$ | $CH_3$ | 2-methyl-6-(ethylthiomethyl)phenyl | 133 |
| 92 | CH | N | $CH_3$ | $CH_3$ | 2-methyl-6-(ethylsulfinylmethyl)phenyl | 178 |
| 93 | CH | N | $CH_3$ | $CH_3$ | 2-methyl-6-(ethylsulfonylmethyl)phenyl | 210 |
| 94 | CH | N | $CH_3$ | $CH_3$ | 2-methyl-6-hydroxyphenyl | 168 |
| 95 | CH | N | $CH_3$ | $CH_3$ | 2-methyl-6-acetoxyphenyl | 185 |

TABLE 1-continued

Examples of compounds of the formula (I)

| Ex. No. | Q¹ | Q² | R¹ | R² | Ar | Melting point (° C.) |
|---|---|---|---|---|---|---|
| 96 | CH | N | $CH_3$ | $CH_3$ | 2-methylphenyl-O-COC(CH₃)₃ | 172 |
| 97 | CH | N | $CH_3$ | $CH_3$ | 2-methylphenyl-O-SO₂CH₃ | 130 |
| 98 | CH | N | $CH_3$ | $CH_3$ | 2-methylphenyl-(1-ethyl-4-phenyl-triazolidine-3,5-dione-2-yl) | 180 |
| 99 | CH | N | $CH_3$ | $CH_3$ | 2-methylphenyl-(1-methyl-4-ethyl-triazolidine-3,5-dione-2-yl) | 163 |
| 100 | CH | N | $CH_3$ | $CH_3$ | 2-methylphenyl-(3-ethyl-4-methyl-5-oxo-triazolin-1-yl) | 208 |
| 101 | CH | N | $CH_3$ | $CH_3$ | 2-methylphenyl-(1-methyl-4-cyclopropyl-triazolidine-3,5-dione-2-yl) | 190 |

TABLE 1-continued
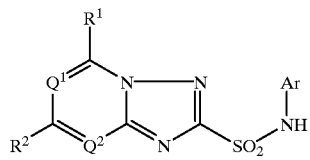
Examples of compounds of the formula (I)
| Ex. No. | Q¹ | Q² | R¹ | R² | Ar | Melting point (° C.) |
|---|---|---|---|---|---|---|
| 102 | CH | N | $CH_3$ | $CH_3$ | 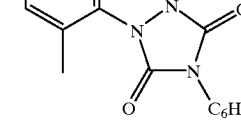 | 200 |
| 103 | CH | N | $CH_3$ | $CH_3$ | 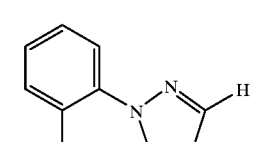 | 228 |
| 104 | CH | N | $CH_3$ | $CH_3$ | 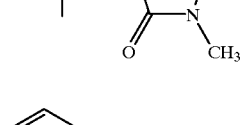 | 233 |
| 105 | CH | N | $CH_3$ | $CH_3$ | 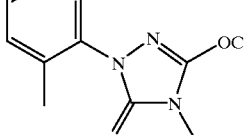 | 226 |
| 106 | CH | N | $CH_3$ | $CH_3$ | 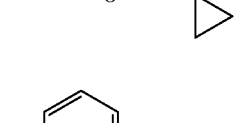 | 168 |
| 107 | CH | N | $CH_3$ | $CH_3$ | 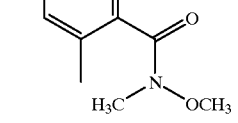 | 195 |

TABLE 1-continued

Examples of compounds of the formula (I)

| Ex. No. | Q¹ | Q² | R¹ | R² | Ar | Melting point (° C.) |
|---|---|---|---|---|---|---|
| 108 | CH | N | CH₃ | CH₃ | 2-methylphenyl-SO₂-N(CH₃)₂ | 105 |
| 109 | CH | N | CH₃ | CH₃ | 2-methylphenyl-SO₂-NH-C(CH₃)₃ | 103 |
| 110 | CH | N | CH₃ | CH₃ | 2-methylphenyl-SO₂-N(C₂H₅)₂ | |
| 111 | CH | N | CH₃ | CH₃ | 2,5-difluoro-4-methyl-benzonitrile | |
| 112 | CH | N | CH₃ | CH₃ | 2-methylphenyl-SO₂-N(C₂H₅)₂ | 188 |
| 113 | CH | N | CH₃ | CH₃ | 2-methyl-1,3-dimethoxybenzene | 243 |
| 114 | CH | N | CH₃ | CH₃ | 2-methylphenyl-O-CHF₂ | 215 |

TABLE 1-continued

Examples of compounds of the formula (I)

| Ex. No. | Q¹ | Q² | R¹ | R² | Ar | Melting point (° C.) |
|---|---|---|---|---|---|---|
| 115 | CH | N | CF₃ | CH₃ | 2-methyl-6-(OCHF₂)phenyl | 158 |
| 116 | CH | N | CH₃ | CH₃ | 4-CF₃-2-methyl-6-Br-phenyl | 211 |
| 117 | CH | N | CH₃ | CH₃ | 2-CF₃-3-Br-6-methyl-phenyl | 192 |
| 118 | CH | N | CH₃ | CH₃ | 3-CH₃-2-methyl-6-(OCHF₂)phenyl | 232 |
| 119 | CH | N | CH₃ | CH₃ | 4-CH₃-2-methyl-6-(OCHF₂)phenyl | 207 |
| 120 | CH | N | CH₃ | CH₃ | 5-CH₃-2-methyl-6-(OCHF₂)phenyl wait | 215 |
| 121 | CH | N | CF₃ | CH₃ | 3-CH₃-2-methyl-6-(OCHF₂)phenyl | 204 |

TABLE 1-continued

Examples of compounds of the formula (I)

(I)

| Ex. No. | Q¹ | Q² | R¹ | R² | Ar | Melting point (° C.) |
|---|---|---|---|---|---|---|
| 122 | CH | N | CF$_3$ | CH$_3$ | 4-methyl-2-methyl-phenyl-O-CHF$_2$ | 163 |
| 123 | CH | N | CF$_3$ | CH$_3$ | 5-methyl-2-methyl-phenyl-O-CHF$_2$ | 163 |
| 124 | CH | N | CH$_3$ | CH$_3$ | 6-chloropyridin-3-yl-CH$_2$- | 204 |
| 125 | CH | N | CF$_3$ | CH$_3$ | 6-chloropyridin-3-yl-CH$_2$- | 155 |
| 126 | CH | N | CH$_3$ | CH$_3$ | 4-bromo-2,6-dimethyl-phenyl (with CH$_3$ para) | 250 |
| 127 | CH | N | CH$_3$ | CH$_3$ | 3-bromo-5-ethyl-phenyl with H$_5$C$_2$ and CH$_3$ substituents | 219 |

TABLE 1-continued

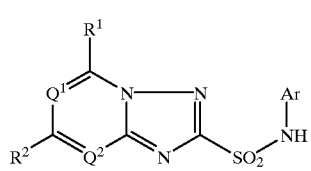

Examples of compounds of the formula (I)

| Ex. No. | $Q^1$ | $Q^2$ | $R^1$ | $R^2$ | Ar | Melting point (° C.) |
|---|---|---|---|---|---|---|
| 128 | CH | N | $CH_3$ | $CH_3$ | 3-Br, 5-$CH_3$, 4-$CH_3$, 2-$C_2H_5$ phenyl | 232 |
| 129 | CN | N | $CH_3$ | $CH_3$ | 3-Br, 5-$CH_3$, 4-$CH_3$, 2-$C(CH_3)_3$ phenyl | 186 |

Use Examples

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After approximately 24 hours, the preparation of active compound is sprayed onto the soil—in such a way as to apply the particular amounts of active compound desired per unit area.

The concentration of the spray liquor is chosen so that the particular desired amounts of active compound are applied in 1000 l of water/ha.

After three weeks, the degree of damage to the plants is rated in % damage by comparison with the development of the untreated control.

The figures denote:

0%=no effect (like untreated control)

100%=total destruction

In this test, for example, the compounds of Preparation Example 4, 5, 6, 13, 14, 17, 18, 19, 22, 23, 25, 34, 35, 38, 39, 43, 60, 63, 73, 74, 75, 76, 77, 82, 84, 85, 104, 115, 118 and 121 show strong activity against weeds (cf. the tables below for Example A), and some of them are tolerated well by crop plants, such as, for example, wheat, soya and cotton.

Tables for Example A
Pre-emergence test/greenhouse

| 1) Compound of Preparation Ex. No. | Application rate (g ai./ha) | Wheat | Alo-pecurus | Bromus | Echino-chloa | Lolium | Galium | Matricaria | Solanum |
|---|---|---|---|---|---|---|---|---|---|
| 13 | 250 | 5 | 100 | — | 100 | 80 | 100 | 100 | 100 |
| 14 | 125 | — | 95 | 95 | 100 | 90 | 70 | 100 | 100 |

| 2) Compound of Preparation Ex. No. | Application rate g ai./ha | Wheat | Alo-pecurus | Cyperus | Digitaria | Echino-chloa | Galium | Matricaria | Solanum |
|---|---|---|---|---|---|---|---|---|---|
| 43 | 125 | 10 | 100 | 100 | 100 | 100 | 100 | 100 | 100 |

-continued

Tables for Example A
Pre-emergence test/greenhouse

| 3) Compound of Preparation Ex. No. | Application rate g ai./ha | Wheat | Alopecurus | Cyperus | Digitaria | Galium | Galinsoga | Matricaria | Solanum |
|---|---|---|---|---|---|---|---|---|---|
| 60 | 500 | 20 | 95 | 100 | 80 | 95 | 95 | 95 | 95 |

| 4) Compound of Preparation Ex. No. | Application rate g ai./ha | Soya | Bromus | Echinochloa | Lolium | Poa | Galium | Galinsoga | Matricaria | Solanum |
|---|---|---|---|---|---|---|---|---|---|---|
| 75 | 1000 | 10 | 80 | 90 | 95 | 95 | 95 | 100 | 95 | 95 |

| 5) Compound of Preparation Ex. No. | Application rate g ai./ha | Cotton | Alopecurus | Digitaria | Echinochloa | Poa | Galinsoga | Matricaria | Solanum |
|---|---|---|---|---|---|---|---|---|---|
| 104 | 250 | 0 | 80 | 90 | 80 | 80 | 90 | 95 | 90 |

| 6) Compound of Preparation Ex. No. | Application rate g ai./ha | Wheat | Soya | Digitaria | Poa | Galinsoga | Matricaria | Solanum |
|---|---|---|---|---|---|---|---|---|
| 115 | 100 | 0 | 0 | 95 | — | 100 | 95 | 90 |
| 121 | 125 | 0 | 0 | — | 70 | 95 | 95 | 90 |

| 7) Compound of Preparation Ex. No. | Application rate g ai./ha | Alopecurus | Bromus | Cyperus | Echinochloa | Lolium | Galium | Matricaria | Solanum |
|---|---|---|---|---|---|---|---|---|---|
| 76 | 500 | 100 | 100 | 100 | 100 | 100 | 100 | 100 | 100 |

| 8) Compound of Preparation Ex. No. | Application rate g ai./ha | Alopecurus | Cyperus | Digitaria | Echinochloa | Galium | Galinsoga | Matricaria | Solanum |
|---|---|---|---|---|---|---|---|---|---|
| 73 | 250 | — | 95 | 95 | 95 | 95 | 95 | 95 | 95 |
| 74 | 250 | 80 | — | 95 | 90 | 90 | 100 | 95 | 95 |

| 9) Compound of Preparation Ex. No. | Application rate g ai./ha | Alopecurus | Cyperus | Echinochloa | Galium | Galinsoga | Matricaria | Solanum |
|---|---|---|---|---|---|---|---|---|
| 5 | 125 | 95 | 90 | 95 | 95 | 95 | 95 | 90 |
| 4 | 125 | 90 | 95 | 90 | 90 | 95 | 95 | 90 |
| 85 | 125 | 90 | 90 | 90 | 90 | 95 | 95 | 90 |
| 84 | 250 | 80 | 95 | 70 | 90 | 95 | 95 | 95 |
| 19 | 250 | 80 | 100 | 95 | — | 95 | 95 | — |
| 6 | 500 | 95 | 90 | 90 | 95 | 95 | 95 | 95 |
| 34 | 250 | 99 | 95 | 90 | 100 | — | 100 | 100 |
| 35 | 250 | 95 | — | 95 | 95 | 100 | 95 | 95 |
| 22 | 250 | 80 | — | 95 | 100 | 100 | 95 | 95 |
| 23 | 250 | — | — | 95 | 100 | 100 | 95 | — |
| 25 | 500 | 80 | 80 | 100 | 100 | — | 100 | 100 |
| 118 | 250 | 80 | 95 | 95 | 90 | 95 | 95 | 95 |

| 10) Compound of Preparation Ex. No. | Application rate g ai./ha | Alopecurus | Digitaria | Echinochloa | Galium | Matricaria | Solanum |
|---|---|---|---|---|---|---|---|
| 82 | 500 | 95 | 95 | 100 | 100 | 100 | 100 |
| 63 | 125 | 100 | 95 | 100 | 100 | 100 | 100 |

| 11) Compound of Preparation Ex. No. | Application rate g ai./ha | Alopecurus | Digitaria | Echinochloa | Poa | Galium | Galinsoga | Matricaria | Solanum |
|---|---|---|---|---|---|---|---|---|---|
| 17 | 250 | 95 | 95 | — | 95 | 95 | 95 | 95 | 95 |
| 18 | 250 | 90 | 90 | 95 | 90 | 95 | 100 | 100 | 95 |

| 12) Compound of Preparation Ex. No. | Application rate g ai./ha | Alopecurus | Galium | Matricaria | Solanum |
|---|---|---|---|---|---|
| 38 | 500 | 80 | 100 | 100 | 95 |
| 39 | 500 | 80 | 100 | 100 | 100 |

-continued

Tables for Example A
Pre-emergence test/greenhouse

| 13) Compound of Preparation Ex. No. | Application rate g ai./ha) | Cyperus | Echinochloa | Lolium | Galium | Matricaria | Solanum |
|---|---|---|---|---|---|---|---|
| 77 | 500 | 95 | 90 | 80 | 95 | 100 | 95 |

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular desired amounts of active compound are applied in 1000 l of water/ha. After three weeks, the degree of damage to the plants is rated in % damage by comparison with the development of the untreated control.

The figures denote:

0%=no effect (like untreated control)

100%=total destruction

In this test, for example, the compounds of Preparation Example 6, 17, 18, 19, 22, 60, 63, 73, 76, 77, 82, 84, 118 and 121 show strong activity against weeds (cf. the tables below for Example B), and without exception they are tolerated well by crop plants, such as, for example, wheat.

Tables for Example B
Post-emergence test/greenhouse

| 1) Compound of Preparation Ex. No. | Application rate (g ai./ha) | Wheat | Abutilon | Datura | Ipomoea | Matricaria | Solanum | Xanthium |
|---|---|---|---|---|---|---|---|---|
| 84 | 125 | 10 | — | 90 | 90 | 80 | 90 | 70 |
| 19 | 1000 | — | 95 | 90 | 95 | 95 | 95 | 100 |
| 6 | 125 | 10 | 95 | 90 | 80 | 90 | 95 | 70 |
| 22 | 500 | 5 | 100 | 95 | 95 | 100 | 90 | 100 |
| 118 | 250 | 10 | 95 | 95 | 95 | 90 | 100 | 100 |
| 73 | 125 | 20 | 95 | 95 | 90 | 100 | 95 | 100 |
| 60 | 125 | 5 | 90 | 90 | 80 | — | 90 | 70 |
| 121 | 500 | 5 | — | 60 | 100 | 70 | 95 | 95 |
| 76 | 500 | 20 | 95 | 70 | 90 | 95 | 95 | 100 |
| 77 | 500 | — | 95 | — | 80 | 100 | 95 | 100 |
| 17 | 30 | 10 | 95 | 90 | 90 | 95 | 90 | 95 |

| 2) Compound of Preparation Ex. No. | Application rate (g ai./ha) | Wheat | Lolium | Sorghum | Datura | Ipomoea | Matricaria | Solanum | Xanthium |
|---|---|---|---|---|---|---|---|---|---|
| 82 | 500 | — | 95 | 95 | 100 | 100 | 100 | 100 | 100 |
| 18 | 125 | 10 | 80 | 80 | 90 | 90 | 100 | 90 | 95 |

| 3) Compound of Preparation Ex. No. | Application rate (g ai./ha) | Alopecurus | Lolium | Sorghum | Datura | Ipomoea | Matricaria | Solanum | Xanthium |
|---|---|---|---|---|---|---|---|---|---|
| 63 | 125 | 90 | 80 | 95 | 95 | 95 | 95 | 100 | 95 |

Example C

Sphaerotheca Test (cucumber)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with conidia of the fungus Sphaerotheca fuliginea.

The plants are subsequently placed in a greenhouse at 23 to 24° C. and at a relative atmospheric humidity of approximately 75%.

Evaluation is carried out 10 days after the inoculation.

In this test, for example, the compounds of Preparation Example 4, 5, 19 and 85 show strong activity (cf. Table C below).

TABLE C

Spaerotheca test (cucumber)/protective

| Active compound | Efficacy in % of the untreated control at an active compound concentration of 100 ppm |
|---|---|
| 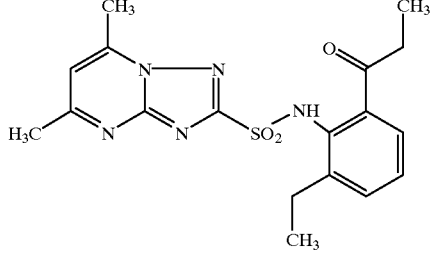 (5) | 100 |
| 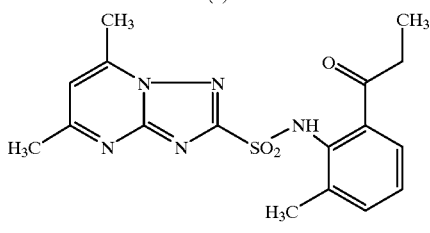 (4) | 92 |
| 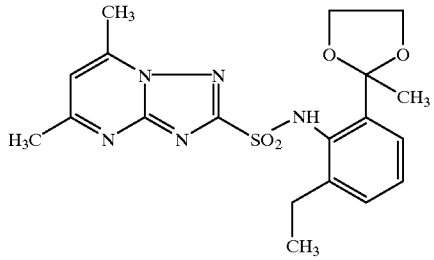 (85) | 95 |
| 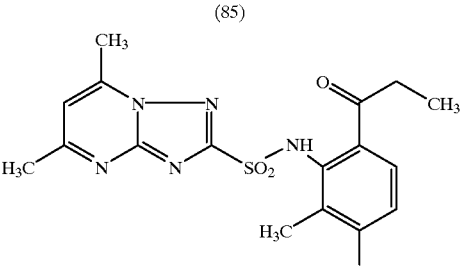 (19) | 100 |

Example D

Podosphaera Test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated by dusting with conidia of the causative organism of apple mildew Podosphaera leucotricha.

The plants are then placed in a greenhouse at 23° C. and a relative atmospheric humidity of approximately 70%.

Evaluation is carried out 10 days after the inoculation.

In this test, for example, the compounds of Preparation Example 4, 5, 19 and 85 show strong activity (cf. Table D below).

TABLE D

Podosphaera test (apple)/protective

| Active compound | Efficacy in % of the untreated control at an active compound concentration of 100 ppm |
|---|---|
| 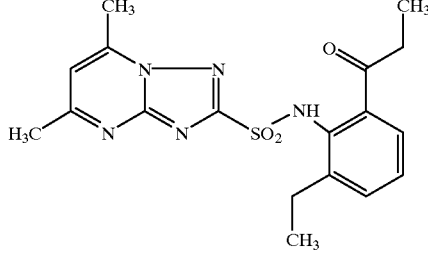<br>(5) | 99 |
| 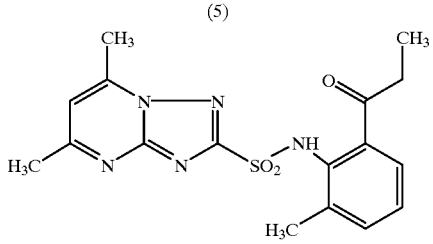<br>(4) | 85 |
| 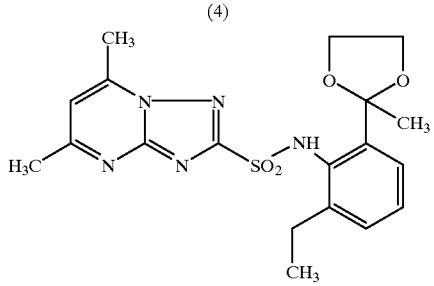<br>(85) | 100 |
| 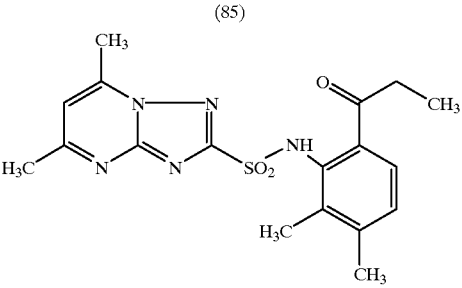<br>(19) | 100 |

Example E

Plutella Test

Solvent: 7 parts by weight of dimethylfornamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are populated with caterpillars of the diamond-back moth (Plutella maculipennis) while the leaves are still moist.

After the desired period of time, the kill in % is determined. 100% means that all caterpillars have been killed; 0% means that none of the caterpillars have been killed.

In this test, for example, the compounds of Preparation Examples 21, 23 and 36 show strong activity (cf. Table E below).

TABLE E (plant damaging insects)
Plutella test

| Active compound | Active compound concentration in % | Kill after 7d |
|---|---|---|
| (36) | 0.1 | 100 |
| (21) | 0.1 | 100 |
| (23) | 0.1 | 100 |

What is claimed is:

1. A substituted triazoloazinesulphonamide of the formula (I)

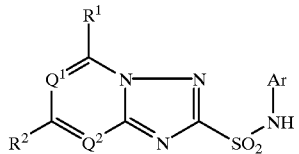

wherein $Q^1$ represents a CH grouping, $Q^2$ represents nitrogen, $R^1$ represents halogen or represents $C_1$–$C_4$-alkyl, $C_1$–$C_4$-alkoxy, $C_1$–$C_4$-alkylthio, $C_1$–$C_4$-alkylamino or di-($C_1$–$C_4$-alkyl)amino, each of which is unsubstituted or substituted by hydroxyl, halogen or $C_1$–$C_4$-alkoxy, $R^2$ represents hydrogen, halogen or represents $C_1$–$C_4$-alkyl, $C_1$–$C_4$-alkoxy, $C_1$–$C_4$-alkylthio, $C_1$–$C_4$-alkylamino or di-($C_1$–$C_4$-alkyl)amino, each of which is unsubstituted or substituted by halogen, and Ar represents wherein $A^{13}$ represents cyano, carbamoyl, 5,6-dihydro-1,4,2-dioxazin-3-yl, halogen, $C_1$–$C_4$-alkyl, $C_1$–$C_4$-alkyl-carbonyl or $C_1$–$C_4$-alkoxy-carbonyl, $A^{14}$ represents hydrogen, represents cyano, cabamoyl, halogen, $C_1$–C4-alkyl, $C_1$–$C_4$-alkylcarbonyl or $C_1$–$C_4$-alkoxy-carbonyl, $A^{15}$ represents hydrogen, represents cyano, carbamoyl, halogen, $C_1$–C4-alkyl, $C_1$–$C_4$-aklylcarbonyl or $C_1$–$C_4$-alkoxy-carbonyl, or together with $A^{14}$ represents a fused benzo grouping, and a salt of the compound of the formula (I), with the following proviso:
i) if $A^{13}$ represents $C_1$–$C_4$-alkoxy-carbonyl then $A^{14}$ and $A^{15}$ cannot both be hydrogen.

2. A compound the formula (I) according to claim 1, wherein $Q^1$ represents a CH grouping, $Q^2$ represents nitrogen, $R^1$ represents fluorine, chlorine, bromine, or represents methyl, ethyl, n- or i-propyl, methoxy, ethoxy, n- or i-propoxy, methylthio, ethylthio, n- or i-propylthio, methylamino, ethylamino, n- or i-propylamino, dimethyl-amino or diethylamino, each of which is unsubstituted or substituted by fluorine, chlorine, methoxy or ethoxy, $R^2$ represents hydrogen, fluorine, chlorine, bromine or represents methyl, ethyl, n- or i-propyl, methoxy, ethoxy, n- or i-propoxy, methylthio, ethylthio, n- or i-propylthio, methylamino, ethylamine, n- or i-propylamino, dimethylamino or diethylamino, each of which is unsubstituted or substituted by fluorine, chlorine, methoxy, or ethoxy, Ar represents

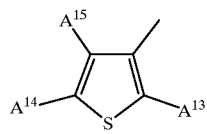

wherein $A^{13}$ represents cyano, carbamoyl, 5,6-dihydro-1,4,2-dioxazin-3-yl, fluorine, chlorine, bromine, methyl, ethyl, n- or i-propyl, acetyl, priopionyl, n- or i-butyroyl, methoxycarbonyl, ethoxycarbonyl, n- or i-propoxycarbonyl, $A^{14}$ represents hydrogen, represents cyano, carbamoyl, fluorine, chlorine, bromine, methyl, ethyl, n- or i-propyl, acetyl, propionyl, n- or i-butyroyl, methoxycarbonyl, ethoxycarbonyl, n- or i-propoxycarbonyl, $A^{15}$ represents hydrogen, represents cyano, carbomoyl, fluorine, chlorine, bromine, methyl, ethyl, n- or i-propyl, acetyl, propionyl, n- or i-butyroyl, methoxycarbonyl, ethoxycarbonyl, n- or i propoxycarbonyl, or together with $A^{14}$ represents a fused benzo grouping, and a salt of the compound of the formula (I) selected from the group consisting of lithium, sodium, potassium, magnesium, calcium, ammonium, $C_1$–$C_4$-alkyl-ammonium, di-($C_1$–$C_4$-alkyl) ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I).

3. A substituted triazoloazinesulphonamide of the formula (I)

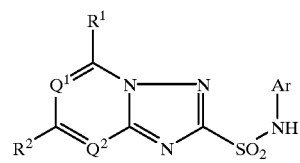

wherein $Q^1$ represents CH $Q^2$ represents N $R^1$ represents $CH_3$ $R^2$ represents $CH_3$, and Ar represents the following formula

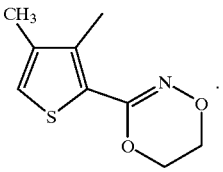

4. A plant treatment composition comprising at least one compound of the formula (I) or one of the salts thereof according to claim 1 and one or more members selected from the group consisting of liquid solvents, solid carriers, emulsifiers, dispersing agents and foam-forming agents.

5. A method for controlling weeds, undesirable microorganisms, arthropods and/or nematodes comprising the step of allowing compounds of the formula (1) or salts thereof according to claim 1 to act on the weeds, the undesirable microorganisms, the arthropods and/or nematodes or their habitat.

* * * * *